(12) United States Patent
Napoletano et al.

(10) Patent No.: US 6,211,387 B1
(45) Date of Patent: Apr. 3, 2001

(54) DIOL COMPOUNDS AS INTERMEDIATES FOR PREPARING ANTIMYCOTIC COMPOUNDS

(75) Inventors: Mauro Napoletano; Marco Villa, both of Milan; Aldo Belli, Cornate d'Adda; Giancarlo Grancini, Nova Milanese; Biase Continanza, Milan, all of (IT)

(73) Assignee: Zambon Group S.p.A., Vincenza (IT)

( * ) Notice: Subject to any disclaimer, the term of this patent is extended or adjusted under 35 U.S.C. 154(b) by 0 days.

(21) Appl. No.: 09/555,509

(22) PCT Filed: Nov. 20, 1998

(86) PCT No.: PCT/EP98/07481

§ 371 Date: Jun. 5, 2000

§ 102(e) Date: Jun. 5, 2000

(87) PCT Pub. No.: WO99/29645

PCT Pub. Date: Jun. 17, 1999

(30) Foreign Application Priority Data

Dec. 5, 1997 (IT) ................................. MI97A2696

(51) Int. Cl.[7] .................................. C07D 315/00
(52) U.S. Cl. .................. 549/423; 556/486; 568/660; 568/662
(58) Field of Search .................. 568/660, 662, 568/811; 556/486; 549/423

(56) References Cited

FOREIGN PATENT DOCUMENTS 0 315 946   5/1989   (EP) .

OTHER PUBLICATIONS

Ishino, Y. et al., "A New Synthesis Of Trans–2–Substituted–2–Butene–1,4–Diols From 2–Butyne–1,4–Diol Via Nucleophilic Addition Of Grignard Reagents", Chemistry Letters, No. 5, 1984, pp. 765–768.

Cohen, T. et al., "Copper–Induced Coupling Of Coupling Of Vinyl Halides", Journal of American Chemical Society, vol. 94, No. 12, 1972, pp. 4363–4364.

Anthony N. De Silva et al., "Grignard Addition Reactions to 1,4–Difunctionalized But–2–ynes", Australian Journal of Chemistry, vol. 46, 1996, pp. 1657–1671.

*Primary Examiner*—Bernard Dentz
(74) *Attorney, Agent, or Firm*—Arent Fox Plotkin Kintner Kahn

(57) ABSTRACT

A compound of formula (II), wherein $R_1$ is chloro, fluoro or trifluoromethyl; $R_2$ is hydrogen, chloro, fluoro or trifluoromethyl; and R is hydrogen or a protective group for the hydroxy moiety useful as an intermediate for the synthesis of antimycotic azole compounnds.

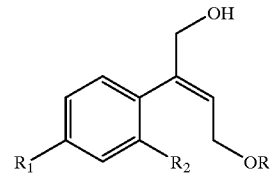

6 Claims, No Drawings

DIOL COMPOUNDS AS INTERMEDIATES FOR PREPARING ANTIMYCOTIC COMPOUNDS

This is a 371 of International Application Ser. No. PCT/EP/98/07481, filed Nov. 20, 1998.

The present invention relates to diol compounds as intermediates useful in the preparation of antimycotic azole compounds.

The compounds of formula I

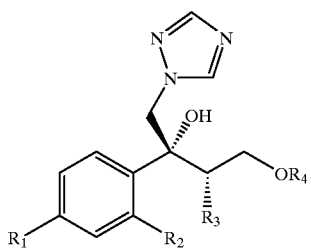

(I)

wherein $R_1$ is chlorine, fluorine or trifluoromethyl;

$R_2$ is hydrogen, chlorine, fluorine or trifluoromethyl;

$R_3$ is $C_{1-4}$ alkyl; and $R_4$ is a polyfluoroalkyl $C_{1-5}$ group containing at least two fluorine atoms and optionally other halogen atoms selected from chlorine and bromine;

and the pharmaceutically acceptable salts thereof, are known as antimycotic and antifungal agents.

The patent application WO 97/31903 (in the Applicant's name) shows a class of compounds where the above compounds of formula I fall, as wide spectrum antimycotics against human and animal pathogenic fungi.

Two preparation processes being a synthetic alternative with respect to the synthetic routes taught by the above said prior art are described in two patent applications filed at the same date of the present one by the Applicant. These two processes use a new intermediate which constitutes the object of the present invention.

Therefore the present invention relates to a compound of formula II

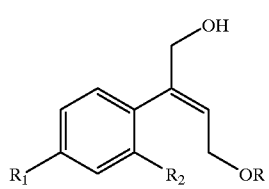

(II)

wherein $R_1$ is chlorine, fluorine or trifluoromethyl;

$R_2$ is hydrogen, chlorine, fluorine or trifluoromethyl; and

R is hydrogen or a protective group for the hydroxy moiety.

The synthesis of the compounds of formula II according to the present invention starts from the iodo- or bromo-benzene derivative of formula III

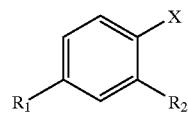

(III)

wherein $R_1$ and $R_2$ are as defined above, and X is bromine or iodine, which is first turned into the corresponding Grignard reactant according to known methods and then into the corresponding phenyl-zinc halide or phenyl-boron acid by treatment with zinc halide, preferably chloride, or with trialkyl borate followed by hydrolysis, which is treated with iodo- or bromo-fumarate, prepared as described in *J. Am. Chem. Soc.* 1972, 94 (12), 4363–4, in the presence of a suitable transition metal(0)-based catalyst. Preferred examples of catalyst are palladium or nickel, optionally supported by ligands such as, for example, triphenylphosphine.

The transition metal(0)-based catalysts may be in case prepared in situ starting from the corresponding salts such as, for example, nickel chloride, cobalt chloride, nickel acetylacetonate, ferric chloride, palladium chloride, lithium tetrachlorocuprate, palladium acetate and palladium acetylacetonate.

Only for practical reasons palladium tetrakis (triphenylphosphine), nickel tetrakis(triphenylphosphine) or palladium on charcoal in the presence of triphenylphosphine are preferred, optionally prepared in situ as described, for example, in Org. Synth., 66, 67–74, 1988.

In this way a diester of formula IV

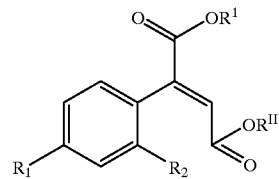

(IV)

wherein $R_1$ and $R_2$ are as defined above, and $R^I$ and $R^{II}$ are independently a $(C_{1-4})$alkyl group, is obtained, which is reduced according to common techniques, for example with diisobutyl-aluminium hydride (DIBAH) to give the compound II wherein R=H.

Another synthetic route for yielding product II starts from the derivative of formula III which, turned into the corresponding Grignard compound and, then, reacted with a diester of oxalic acid, gives the compound of formula V

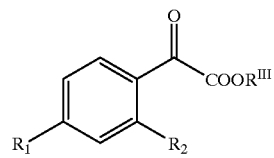

(V)

wherein $R_1$ and $R_2$ are as defined above, and $R^{III}$ is a $(C_{1-4})$alkyl group, which is reacted in the presence of a base such as, for example, sodium ethylate or methylate, optionally prepared in situ, or sodium hydride, according to the procedures of the so-called Wittig reaction, for example with trialkyl phosphonoacetate.

It is thereby obtained the compound of formula IV which is turned into the compound of formula II wherein R=H as already explained above.

It is intended that the product of formula II wherein R is a protective group of the hydroxy moiety may also be obtained by reacting a compound of formula II wherein R is hydrogen with a protective group of the alcoholic function (see, for example, T. W. Greene and P. G. M. Wuts, Protective groups in organic synthesis, John Wiley & Sons, New York).

Preferred protective groups according to the present invention are those stable in the presence of bases and nucleophilic reactants, in particular silyl ethers, benzyl ether, 2-methoxy-ethoxy-methyl ether, methoxy-methyl ether and tetrahydropyranyl ether.

A further method for yielding the product II entails the reaction of the magnesium derivative of the compound of formula III with the diol of formula VI

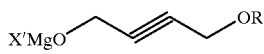
(VI)

wherein X' is a halogen atom and R is as defined above or is a MgX' group.

Hereinbelow fulfilment examples of the present invention are provided.

EXAMPLE 1

Synthesis of (E)-2-(2,4-dichlorophenyl)-butendioic acid diethyl ester a) with catalyst prepared in situ from Pd(OAc)$_2$+PPh$_3$ A suspension of magnesium (1.82 g; 0.075 moles) kept under stirring at 25° C. in ethyl ether (20 ml) was added with ethyl bromide (50 mg). After 15 minutes 1,3—dichloro-4-iodobenzene (13.65 g; 0.05 moles) in ethyl ether (20 ml) was added in about 1 hour at the temperature of 18–22° C., and at the end of the addition the stirring was kept on at 20° C. for further 90 minutes. The metallic magnesium was decanted and the surnatant solution was added in 10 minutes to a suspension of dry zinc chloride (13.6 g; 0.1 mole) in ethyl ether (20 ml). The suspension was stirred at room temperature for 90 minutes, then cooled to 0° C., added with dry DMF (40 ml) then with palladium acetate (168 mg; 0.75 mmoles) and triphenylphosphine (395 mg; 1.5 mmoles) and at last a solution of diethyl iodo-fumarate (10.45 g; 0.035 moles), prepared according to *J. Am. Chem. Soc.* 1972, 94 (12), 4363–4, in DMF (10 ml) was dropped in about 30 minutes. The mixture was stirred at room temperature overnight, then cooled to 0° C. added with IN HCl (80 ml) and twice extracted with hexane (80 ml) The organic phases were anhydrified over Na$_2$SO$_4$ and evaporated to dryness. The residue (13 g) was purified by flash chromatography (SiO$_2$; hexane/ethyl ether 95/5) to give 7.82 g of pure (E)-2-(2,4-dichlorophenyl)-butendioic acid diethyl ester (yield: 70% calculated with respect to the diethyl iodo-fumarate).

b) with catalyst prepared in situ from preformed PdCl$_2$ (PPh$_3$)$_2$

A suspension of magnesium (0.73 g, 0.03 moles) in ethyl ether (20 ml) under nitrogen flow was added with ethyl bromide (50 mg). The solution was stirred for 15 minutes then added with a solution of 1,3-dichloro-4-iodobenzene (5.45 g, 0.02 moles) in ethyl ether (10 ml) in 1 hour keeping the temperature at 18–22° C. At the end of the addition the suspension was kept under stirring for 90 minutes at 18–22° C., then decanted and the surnatant added in 10 minutes to a suspension of dry zinc chloride (5.4 g, 0.04 moles) in ethyl ether (8 ml). At the end of the addition the stirring was kept on at 20° C. for further 90 minutes, then cooled to 0° C. DMF (10 ml) and palladium dichloride triphenylphosphine (351 mg, 0.0005 moles), then a solution of diethyl iodo-fumarate (4.18 g, 0.014 moles) in DMF (4 ml) were added. The mixture was kept under stirring for 15 hours at 25° C. and after a work-up similar to the one of point a) 2.1 g of (E)-2-(2,4-dichlorophenyl)-butendioic acid diethyl ester were yielded (yield: 63% calculated with respect to the iodo-fumarate).

$^1$H-NMR (200 MHz, CDCl$_3$, δ=ppm, J=Hz): 1.10 (t, 3H, J=7.1); 1.25 (t, 3H, J=7.1); 4.05 (q, 2H, J=7.1); 4.24 (q, 2H, J=7.1); 7.09 (s, 1H); 7.07–7.42 (m, 3H).

EXAMPLE 2

Synthesis of (2,4-dichloro-phenyl)-oxo-acetic acid ethyl ester

A suspension of magnesium (6.7 g; 0.275 moles) in ethyl ether (125 ml) under stirring and nitrogen flow was added with ethyl bromide (180 mg). A solution of 1,3-dichloro-4-iodobenzene (50 g; 0.183 moles) and ethyl bromide (180 mg) in ethyl ether (100 ml) was dropped in about 1 hour keeping the temperature at 15–20° C. The suspension was stirred for further 2 hours. After decanting the magnesium in excess, the solution was dropped in about 1 hour in a solution of diethyloxalate (29.32 g; 0.2 moles) in ethyl ether (125 ml) cooled to –70° C. At the end of the addition it was stirred at –70° C. for 1 hour, then the temperature was left to rise to 10° C. and the stirring was kept on for another hour. The suspension was added with a saturated solution of NH$_4$Cl (125 ml), the phases were separated and the aqueous one extracted with ethyl acetate (50 ml). The organic phases were washed with a solution of sodium bisulfite and treated with discolouring charcoal. After filtration, the organic solution was distilled under vacuum to give a crude which was purified by chromatography (SiO$_2$; hexane/ethyl ether 9/1) to give 36.2 g of (2,4-dichloro-phenyl)-oxo-acetic acid ethyl ester (yield 80%) as a colourless oil.

$^1$H-NMR (200 MHz, CDCl$_3$, δ=ppm, J=Hz): 1.37 (t, 3H, J=7.2); 4.39 (q, 2H, J=7.2); 7.37 (dd, 1H); 7.45 (d, 1H, J=2.0); 7.70 (d, 1H, J=8.4).

EXAMPLE 3

Synthesis of (E)2-(2,4-dichlorophenyl)-butendioic acid diethyl ester

An ethanolic solution of sodium ethylate, obtained from sodium (3.35 g; 0.1457 moles) and dry ethanol (276 ml), kept under stirring in inert atmosphere, was added at 20° C. with a solution of (2,4-dichloro-phenyl)-oxo-acetic acid ethyl ester obtained as described in example 2 (36 g; 0.147 moles), and triethyl phosphonoacetate (34.2 g; 0.152 moles) in dry ethanol (70 ml). The reaction mixture was then brought and kept at reflux for 16–20 hours. After cooling to 25° C., the mixture was poured under stirring into a solution of saturated NaCl (500 ml), ethyl ether was added (150 ml) and the phases were separated. The aqueous phase was extracted again with ethyl ether (150 ml). The joined organic phases were washed with water (100 ml), anhydrified over dry Na$_2$SO$_4$, evaporated to dryness. The thus obtained residue was purified by chromatography (SiO$_2$; hexane/ethyl ether 9/1) to give 24.6 g of (E) 2-(2,4-dichlorophenyl)-butendioic acid diethyl ester (yield 53%) as a colourless oil.

EXAMPLE 4

Synthesis of (E)-2-(2,4-dichlorophenyl)-buten-1,4-diol

A solution of (E)-2-(2,4-dichlorophenyl)-butendioic acid diethyl ester (3.2 g; 0.01 moles) obtained as described in example 1 or 3, in toluene (32 ml) cooled to a −20° C. under nitrogen, was added in about 90 minutes with 1.2M DIBAH in toluene (35 ml; 0.042 moles). The mixture was stirred at −20° C. for 1 hour, then slowly poured into 1N HCl (170 ml) while keeping the temperature at 0–5° C. After 15 minutes the stirring was halted and the phases left to separate. The aqueous one was isolated and extracted again in toluene (30 ml). The organic phases were washed with water (50 ml), anhydrified over dry $Na_2SO_4$, dried. The crude was purified by flash chromatography ($SiO_2$; hexane/ethyl acetate/methanol 70/30/2) to give 1.45 g of (E)-2-(2,4-dichlorophenyl)-buten-1,4-diol (yield 62%) which was crystallized from isopropyl ether. m.p. 94–95° C.

$^1$H-NMR (300 MHz, DMSO, δ=ppm, J=Hz): 3.66 (dd, 2H, J=6.10, J=5.31); 4.02 (dd, 2H, J=5.62, J=1.41); 4.62 (t, 1H, J=5.31); 5.08 (t, 1H, J=5.62); 5.90 (tt, 1H, J=6.10, J=1.41); 7.23 (d, 1H, J=8.10); 7.43 (dd, 1H, J=8.10, J=2.00); 7.63 (d, 1H, J=2.00).

EXAMPLE 5

Synthesis of (E) (2,4-dichlorophenyl)-2-buten-1.4-diol

A suspension under nitrogen of magnesium (0.8 g; 32.7 mmoles) in ethyl ether (17 ml) kept at 20° C. under stirring, was added with ethyl bromide (25 mg). After 15 minutes a solution of 1,3-dichloro4-iodobenzene (5.95 g; 21.8 mmoles) and ethyl bromide (25 mg) in dry ether (13 ml) was dropwise added (about 1 hour) keeping the temperature at 15–20° C. At the end of the dropping the suspension was kept at 15–20° C. for 2 hours more. The magnesium in excess was removed and the obtained solution was dropped, keeping the temperature at 0–5° C., in a second flask containing a suspension formerly prepared. Such suspension was obtained by adding, at 0–5° C., a THF solution of 3M methyl magnesium chloride (9.6 ml; 29 mmoles) to a solution of 2-butin-1,4-diol (1.25 g; 14.5 mmoles) in THF (30 ml). At the end of the addition the suspension was refluxed and stirred at mild reflux for 24 hours. After cooling to 0° C., an aqueous solution of saturated $NH_4Cl$ was added, the phases were divided and the aqueous one extracted in ether (30 ml). The joined organic phases were washed with water (30 ml), anhydrified over dry $Na_2SO_4$, dried. The product was purified by flash chromatography ($SiO_2$; petrolatum/ethyl acetate 60/40) to give 0.24 g of (E) (2,4dichlorophenyl)-2-buten-1,4-diol (yield 7,3%). The $^1$H-NMR effected on the product is practically the same of the one reported in example 4.

What is claimed is:

1. A compound of formula II

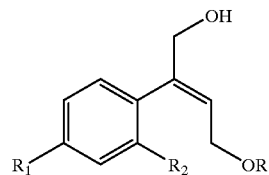

(II)

wherein $R_1$ is chlorine, fluorine or trifluoromethyl;

$R_2$ is hydrogen, chlorine, fluorine or trifluoromethyl;

and R is a protective group for the hydroxy moiety.

2. A compound of formula II according to claim 1 wherein the protective group is one stable in the presence of bases and nucleophilic reactants.

3. A compound of formula II according to claim 1 wherein the protective group for R is selected from the group consisting of silyl ethers, benzyl ether, 2-methoxy-ethoxy-methyl ether, methoxy-methyl ether and tetrahydropyranyl ether.

4. Process for the preparation of a compound of formula II according to claim 1 wherein in addition R may be hydrogen characterized in that a iodo- or bromo-benzene derivative of formula III

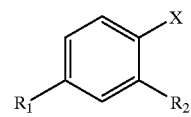

(III)

wherein $R_1$ and $R_2$ are as defined in claim 1, and X is iodine or bromine is first turned into the corresponding Grignard compound and sequentially by treatment with zinc halide or with a trialkyl borate followed by hydrolysis, to the corresponding phenyl-zinc halide or phenyl-boron acid respectively, which is treated with iodo- or bromo-fumarate in the presence of a suitable transition metal(0)-based catalyst, preformed or prepared in situ, thereby yielding a diester of formula IV

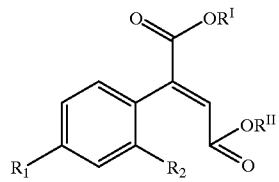

(IV)

wherein $R_1$ and $R_2$ are as defined above, and $R^I$ and $R^{II}$ are independently a $(C_{1-4})$alkyl group, which is reduced to give a compound of formula II wherein R is hydrogen, such substituent being then optionally turned into a protective group of the hydroxy moiety.

5. Process for the preparation of compounds of formula II according to claim 1 wherein in addition R may be hydrogen characterized in that a iodo- or bromo-benzene derivative of formula III

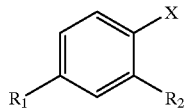 (III)

wherein R₁ and R₂ are as defined in claim 1, and X is iodine or bromine, is turned into the corresponding Grignard compound and, sequentially, reacted with a diester of oxalic acid to give the compound of formula V

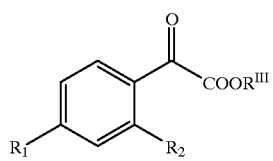 (V)

wherein R₁ and R₂ are as defined above, and $R^{III}$ is a $C_{1-4}$ alkyl group, which is reacted in the presence of a base with trialkyl phosphonoacetate to give the compound of formula IV which is reduced to give the compound of formula II wherein R is hydrogen, such substituent being then optionally turned into a protective group of the hydroxy moiety.

6. Process for the preparation of a compound of formula II according to claim 1 characterized in that an iodo- or bromo-benzene derivative of formula III

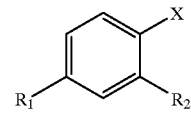 (III)

wherein R₁ and R₂ are as defined in claim 1, and X is iodine or bromine, is turned into the corresponding Grignard compound and, sequentially, reacted with a compound of formula

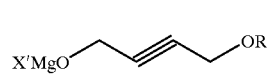 (VI)

wherein X' is a halogen atom and R is as defined in claim 1, or is hydrogen or is a MgX' group.

* * * * *